(12) United States Patent
O'Dwyer et al.

(10) Patent No.: US 11,543,402 B2
(45) Date of Patent: Jan. 3, 2023

(54) IMPEDANCE MEASUREMENT IN DIAGNOSTIC TESTING

(71) Applicant: Analog Devices, Inc., Norwood, MA (US)

(72) Inventors: Thomas G. O'Dwyer, Arlington, MA (US); Gaurav Vohra, Sudbury, MA (US); Xin Zhang, Acton, MA (US); YounJae Kook, Winchester, MA (US); Isaac Chase Novet, Carlsbad, CA (US); Venugopal Gopinathan, Boston, MA (US)

(73) Assignee: Analog Devices, Inc., Norwood, MA (US)

( * ) Notice: Subject to any disclaimer, the term of this patent is extended or adjusted under 35 U.S.C. 154(b) by 207 days.

(21) Appl. No.: 16/757,202

(22) PCT Filed: May 4, 2018

(86) PCT No.: PCT/US2018/031241
§ 371 (c)(1),
(2) Date: Apr. 17, 2020

(87) PCT Pub. No.: WO2019/078922
PCT Pub. Date: Apr. 25, 2019

(65) Prior Publication Data
US 2021/0123902 A1 Apr. 29, 2021

Related U.S. Application Data

(60) Provisional application No. 62/574,667, filed on Oct. 19, 2017.

(51) Int. Cl.
*G01R 33/09* (2006.01)
*G01N 33/487* (2006.01)
(Continued)

(52) U.S. Cl.
CPC ..... *G01N 33/48707* (2013.01); *G01N 27/028* (2013.01); *G01N 33/49* (2013.01);
(Continued)

(58) Field of Classification Search
CPC .... G01N 27/028; G01N 33/49; G01N 33/493; G01N 27/12; G01N 27/227; G01N 33/48707
See application file for complete search history.

(56) References Cited

U.S. PATENT DOCUMENTS

| | | |
|---|---|---|
| 6,264,825 B1 | 7/2001 | Blackburn et al. |
| 2006/0226030 A1 | 10/2006 | Hanke et al. |

(Continued)

FOREIGN PATENT DOCUMENTS

EP 1764418 3/2007

OTHER PUBLICATIONS

International Search Report and Written Opinion issued in International Patent Application Serial No. PCT/US18/31241 dated Aug. 19, 2018, 17 pages.

*Primary Examiner* — Alesa Allgood
(74) *Attorney, Agent, or Firm* — Akona IP PC

(57) ABSTRACT

An impedance measurement system for detecting an analyte in a sample is disclosed. The system includes first, second, and third electrodes, wherein at least a portion of the third electrode is positioned between the first and second electrodes, means for generating an electromagnetic field between the first and second electrodes, means for electrically controlling the third electrode, wherein the third electrode modifies the electromagnetic field, and a processor for detecting a presence of the analyte in the sample, based at least in part on a property of the electromagnetic field.

20 Claims, 17 Drawing Sheets

(51) Int. Cl.
*G01N 27/02* (2006.01)
*G01N 33/49* (2006.01)
*G01N 33/493* (2006.01)
G01N 27/12 (2006.01)
G01N 27/22 (2006.01)

(52) U.S. Cl.
CPC .......... *G01N 33/493* (2013.01); *G01N 27/12* (2013.01); *G01N 27/227* (2013.01)

(56) References Cited

U.S. PATENT DOCUMENTS

| | | |
|---|---|---|
| 2010/0188110 A1 | 7/2010 | Sun |
| 2012/0228155 A1 | 9/2012 | Clare et al. |
| 2013/0053268 A1 | 2/2013 | Frederix et al. |
| 2014/0057283 A1 | 2/2014 | Wang et al. |
| 2014/0106338 A1 | 4/2014 | Fischer |
| 2014/0170645 A1* | 6/2014 | Jovanovich .......... C12Q 1/6806 435/6.11 |
| 2015/0276637 A1* | 10/2015 | Prasad ................ G01N 27/028 506/9 |
| 2018/0191306 A1* | 7/2018 | Ivanov ................ H03F 3/45179 |
| 2020/0138344 A1* | 5/2020 | Ben-Yoav .......... A61B 5/14507 |

\* cited by examiner

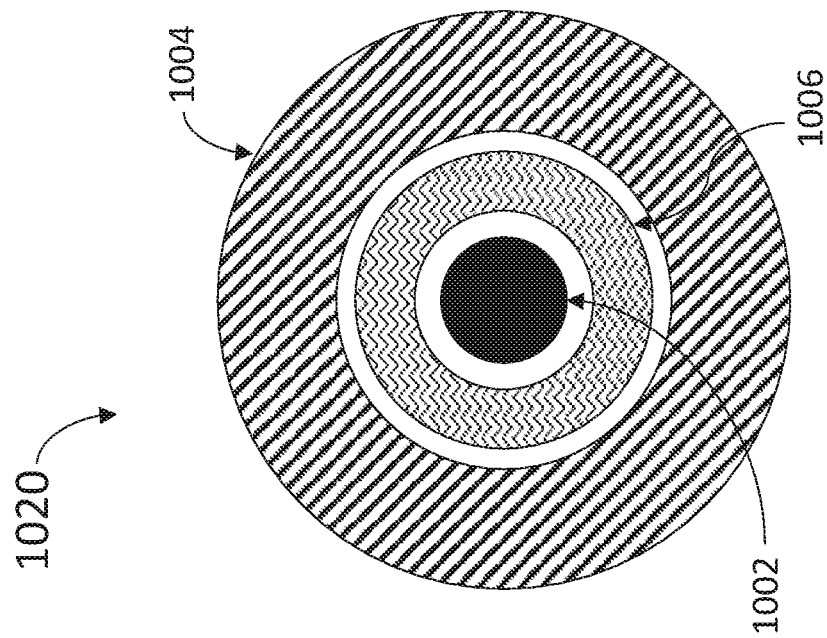
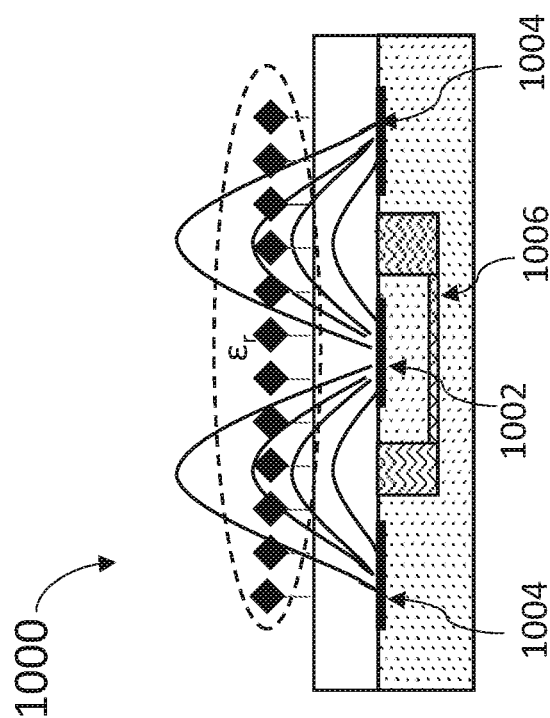

IMPEDANCE MEASUREMENT IN DIAGNOSTIC TESTING

CROSS-REFERENCE TO RELATED APPLICATIONS

This Application claims priority to PCT/US2018/03124, filed May 4, 2018, which also claims priority to U.S. Patent Application Ser. No. 62/574,667, filed Oct. 19, 2017, both applications are hereby incorporated by reference in their entirety into the disclosure of this Application.

TECHNICAL FIELD OF THE DISCLOSURE

The present invention relates to the field of impedance measurement, and in particular to measuring impedance in diagnostic testing.

BACKGROUND

Diagnostic testing can include detection of various analytes in a sample such as urine, blood, or saliva. In one example, the analyte is a virus. A detection device includes a binding element on its surface, and the binding element is designed to bind to the analyte of interest. In one example, an antibody designed to mate with a virus of interest is anchored to the surface of the detection device. The sample is introduced to the detection device, and after a selected period of time, the sample may be removed. If the analyte of interest is present in the sample, then after the sample is removed, the analyte of interest will remain bound to the binding elements. The detection device can then be examined to determine whether any analyte of interest is bound to the device. One way to examine the detection device is via electrical impedance.

FIG. 1 shows an electrical impedance detection device 100 including first 102 and second 104 electrodes. The first 102 and second 104 electrodes are positioned between first 114 and second 116 layers of glass. The electrodes 102 and 104 are coupled to a voltage source 108 and an ammeter 106. The voltage source 108 can apply a voltage between the first 102 and second 104 electrodes. The ammeter 106 measures the current at the first electrode 102. When a voltage is applied to the first electrode 102, an electric field is introduced, as illustrated by electric field lines 112 between the first 102 and second 104 electrodes. The ammeter 106 can be used to measure current and thereby determine the impedance between the first 102 and second 104 electrodes.

The first layer of glass 114 includes binding elements 110 on a top surface, where the binding elements are selected to bind to an analyte of interest. Binding events at the binding elements 110 change the permittivity (E, of the local area, thereby affecting electric fields between the first 102 and second 104 electrodes. However, as shown in FIG. 1, the highest density of electric field lines between the first 102 and second 104 electrodes occur directly between the first 102 and second 104 electrodes, in a region of no interest. Only secondary (or fringing) electric fields extend up to the surface of the first layer of glass 114, where the binding elements 110 are located. Thus, only the secondary electric fields are affected by the change in permittivity ($\varepsilon_r$) caused by binding events at the binding elements 110. Thus, using the detection device 100, even a large change in permittivity will cause only a small change in the capacitance measured at the first 102 and second 104 electrodes.

It is desirable to design a detection device that maximizes the sensitivity of electrical impedance measurements to be able to detect smaller or fewer binding events on the top surface of the device.

OVERVIEW

Systems and methods for measuring impedance in diagnostic testing are disclosed. In particular, a high sensitivity directional impedance measurement system and methods are provided. An impedance measurement system for detecting an analyte in a sample is disclosed. The system includes a substrate for receiving the sample, first, second, and third electrodes, wherein at least a portion of the third electrode is positioned between the first and second electrodes, a voltage source, coupled to the first electrode, wherein the voltage source generates an electromagnetic field between the first and second electrodes, an amplifier configured to generate gain at the third electrode, wherein the gain at the third electrode modifies the electromagnetic field, and a processor for detecting a presence of the analyte in the sample, based at least in part on a property of the electromagnetic field. In some implementations, the gain is negative. The gain may be attenuation.

According to various implementations, an impedance measurement system to detect an analyte in a sample includes first, second, and third electrodes, wherein at least a portion of the third electrode is positioned between the first and second electrodes, means for generating an electromagnetic field between the first and second electrodes, means for electrically controlling the third electrode, wherein the third electrode modifies the electromagnetic field, and a processor for detecting a presence of the analyte in the sample, based at least in part on a property of the electromagnetic field. In some implementations, the processor is further configured to measure a property of the analyte.

In some implementations, the means for generating an electromagnetic field between the first and second electrodes is one of a voltage source and a current source. In some implementations, the means for electrically controlling the third electrode is an amplifier. In further implementations, the means for electrically controlling the third electrode is an impedance device. In some examples, the impedance device is at least one of a resistor and a capacitor. In some examples, the impedance device includes one of a resistive digital-to-analog converter and a capacitive digital-to-analog converter.

In some implementations, the impedance measurement system further includes an ammeter for measuring a current on the first electrode, wherein the processor detects the presence of the analyte based in part on the current measurement. In some implementations, the means for electrically controlling the third electrode adjusts a gain of the third electrode based at least in part on the current measurement.

In some implementations, the impedance measurement system further includes a voltmeter for measuring a voltage at the first electrode, wherein the processor detects the presence of the analyte based in part on the voltage measurement. In some examples, the means for electrically controlling the third electrode adjusts a gain of the third electrode based at least in part on the voltage measurement.

According to various implementations, an impedance measurement system to detect an analyte in a sample includes first, second, and third electrodes, wherein at least a portion of the third electrode is positioned between the first and second electrodes, a voltage source, coupled to the first electrode, wherein the voltage source generates an electromagnetic field between the first and second electrodes, a circuit element configured to adjust a gain at the third electrode, wherein the gain at the third electrode modifies the electromagnetic field, and a processor for detecting a presence of the analyte in the sample, based at least in part on a property of the electromagnetic field. In some implementations, the processor is further configured to measure a property of the analyte.

In some implementations, the circuit element is configured to adjust the gain at the third electrode is one of an amplifier and an impedance device. In some examples, the impedance device is at least one of a resistor and a capacitor.

In some implementations, the impedance measurement system further includes an ammeter for measuring a current on the first electrode, wherein the processor detects the presence of the analyte based in part on the current measurement. In some examples, the circuit element is configured to adjust the gain at the third electrode adjusts the gain based at least in part on the current measurement.

In some implementations, the impedance measurement system further includes a voltmeter for measuring a voltage at the first electrode, wherein the processor detects the presence of the analyte based in part on the voltage measurement. In some examples, the circuit element configured to adjust the gain at the third electrode adjusts the gain based at least in part on the voltage measurement.

According to various implementations, a method detecting an analyte in a sample using impedance measurements, includes receiving the sample at a detection device, generating an electromagnetic field between first and second electrodes in the detection device, electrically controlling a third electrode in the detection device to modify the electromagnetic field, and detecting a presence of the analyte in the sample, based at least in part on a property of the electromagnetic field.

According to various implementations, an impedance measurement system to detect an analyte in a sample includes a matrix of impedance measurement sensor cells, a row processing circuit for providing an input signal to at least one of the sensor cells, wherein the input signal activates the at least one of the sensor cells, a column processing circuit for receiving the output from the sensor cells and generating a system output, and a processor for detecting a presence of the analyte in the sample, based at least in part on the system output. Each sensor cell in the matrix has first, second, and third electrodes, wherein at least a portion of the third electrode is positioned between the first and second electrodes.

In some implementations, the input signal is a voltage source that generates an electromagnetic field. The voltage source generates an electromagnetic field between the first and second electrodes of the at least one of the sensor cells to which the input signal is provided. In some examples, the row processing circuit includes a circuit element configured to adjust a gain at the third electrode of the at least one of the sensor cells, wherein the gain at the third electrode modifies the electromagnetic field. In some implementations, the system output is based at least in part on a property of the electromagnetic field. In some implementations, the processor is further configured to measure a property of the analyte.

BRIEF DESCRIPTION OF THE DRAWING

To provide a more complete understanding of the present disclosure and features and advantages thereof, reference is made to the following description, taken in conjunction with the accompanying figures, wherein like reference numerals represent like parts, in which:

FIGS. 10A-10D show layouts for an impedance measurement system, according to some embodiments of the disclosure.

DESCRIPTION OF EXAMPLE EMBODIMENTS OF THE DISCLOSURE

A high sensitivity directional impedance measurement system and methods are provided. In particular, a detection device including three electrodes is provided, wherein the third electrode is positioned between the first and second electrodes, essentially steering the electric field lines up to an area of the device including the binding elements, thereby improving the sensitivity of the detection device.

As discussed above, in diagnostic systems, an analyte is typically bound to a binding element on a surface of the device. The binding event can be detected by measuring the change in permittivity between two electrodes. A third electrode is used to control and steer the electric field between the two electrodes to maximize the sensitivity to the change in permittivity in a particular region where the binding event occurs.

Figure 2A:
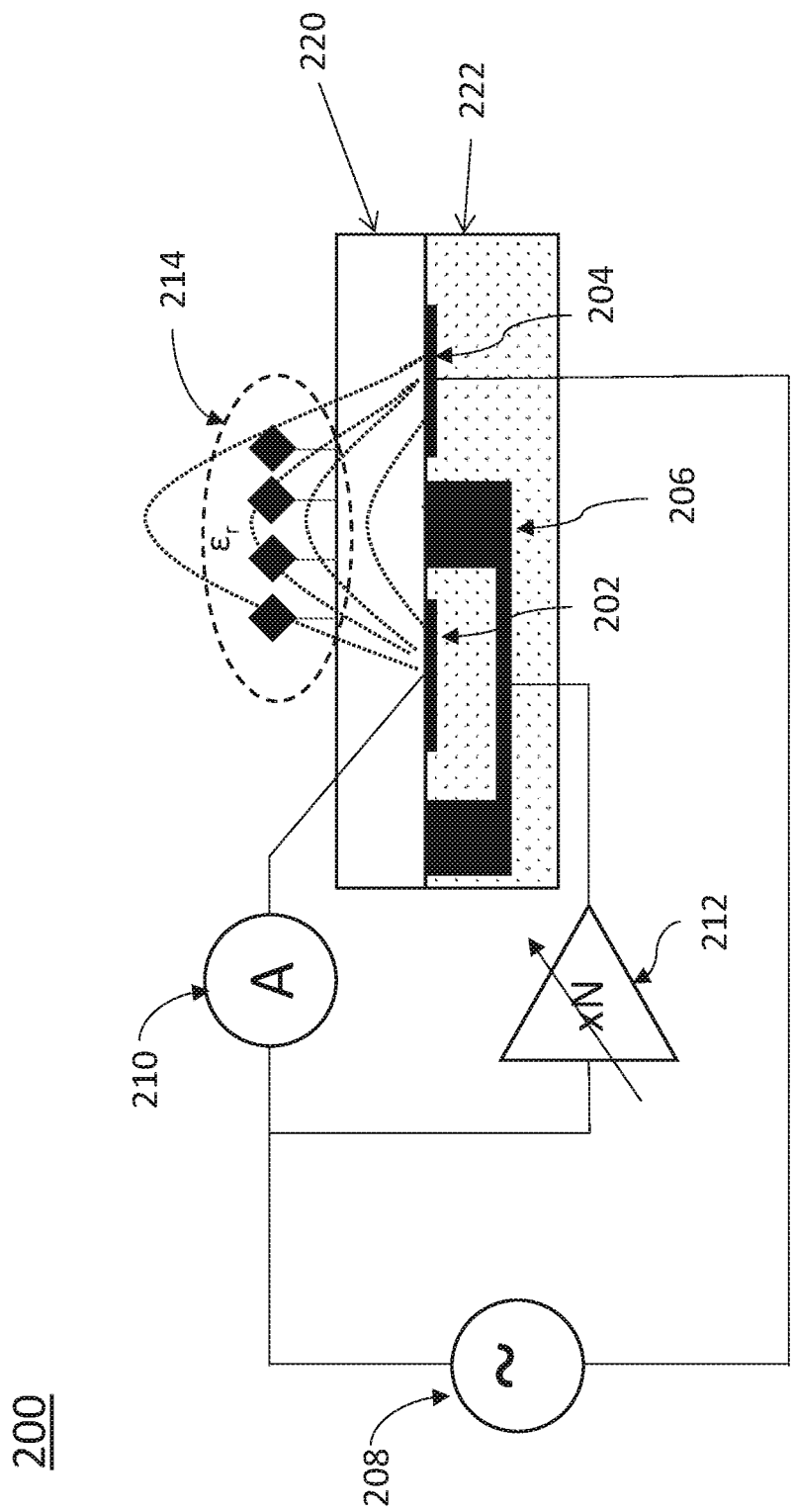
FIG. 2A is a diagram illustrating an impedance measurement system including three nodes, according to some embodiments of the disclosure.

FIG. 2A is a diagram illustrating an impedance measurement system 200 including first 202, second 204, and third 206 nodes, according to some embodiments of the disclosure. The first 202, second 204, and third 206 nodes are positioned in a second layer 222, with the third node 206 positioned at least partially between the first 202 and second 204 nodes. A first layer 220 is positioned on top of the second layer 222. A top surface of the first layer 220 includes binding elements 214.

A voltage source 208 is coupled to the first 202 and second 204 nodes. An ammeter 210 is positioned between the voltage source 208 and the first node 202. An amplifier 212 is connected to the third node 206, the voltage source 208, and the ammeter 210.

In one implementation, a voltage is applied to the first node 202 by the voltage source 208, and the current at the first node is measured by the ammeter 210. The presence of the third node 206 eliminates the electric field lines directly between the first 202 and second 204 nodes. The amplifier 212 can be used to adjust the gain at the third node 206, thereby adjusting the extent of warping of the electric field lines between the first 202 and second 204 nodes. In one example, a higher gain steers the electric field lines further upwards. In some implementations, the amplifier 212 is a variable gain amplifier. In various implementations, the amplifier 212 can be adjusted to control and optimize the electric field lines. In some examples, the amplifier 212 is adjusted to optimize the electric field lines.

Figure 2B:
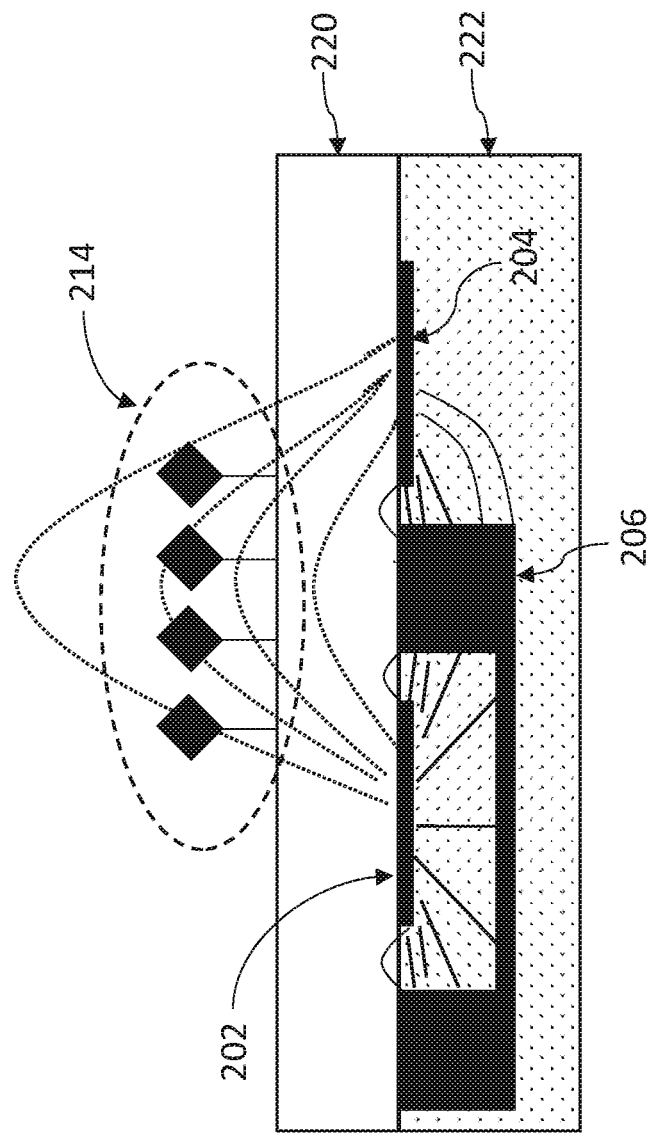
FIG. 2B is a diagram illustrating electric field lines in an impedance measurement system including three nodes, according to some embodiments of the disclosure.

Using a third electrode 206 in a two electrode measurement system, the electric field can be controlled to maximize the sensitivity of the permittivity measurement in a selected region. FIG. 2B is a diagram illustrating electric field lines in an impedance measurement system including three nodes, including electric field lines between the first 202 and third 206 nodes, and electric field lines between the third 206 and second 204 nodes, and electric field lines between the first 202 and second 204 nodes, according to some embodiments of the disclosure. Because the system 200 measures the electric field from the first node 202 to the second node 204, the other electric fields created by the addition of the third node 206 are not included in the measurement.

The electric field created at a particular location (e.g., the location of the binding elements) by two charges (e.g., a first charge from the first node 202 and a second charge from a second node 204) is the vector sum of the force from the first charge and the force from the second charge. The strength of the electric field at the particular location from the first charge is proportional to the inverse distance between the first charge and the location ($kq_1/r^2$, where k is a constant, $q_1$ is the first charge, and r is the distance between the particular location and the first charge). The strength of the electric field at the particular location from the second charge is proportional to the inverse distance between the second charge and the location ($kq_2/r^2$, where k is a constant, $q_2$ is the second charge, and r is the distance between the particular location and the second charge). A vector has a magnitude and a direction, and the electric field at the particular location is the vector sum of the of the force from the first charge and the force from the second charge. When a third charge is added between the first and second charges, another vector is added to the previous two vectors, changing the angle and the strength of the electric field. Thus, the third charge can be manipulated to change the magnitude and angle of the electric field.

Figure 3:
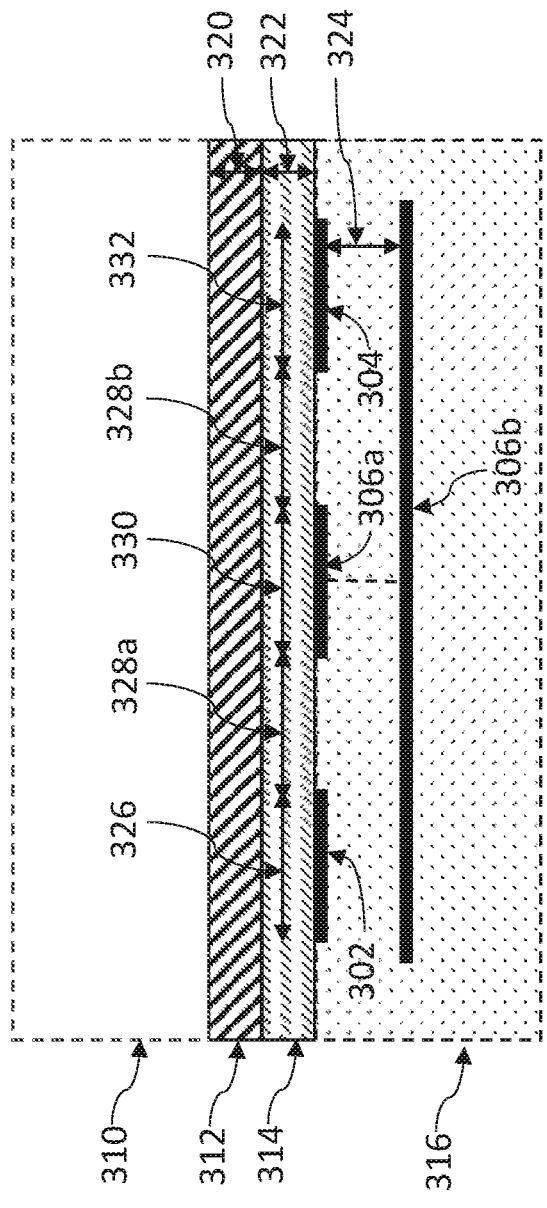
FIG. 3 is a diagram illustrating another impedance measurement system including three nodes, according to some embodiments of the disclosure.

FIG. 3 is a diagram illustrating another impedance measurement system 300 including three nodes, according to some embodiments of the disclosure. In particular, the system 300 includes a first node 302, a second node 304, and a third node including an upper portion 306a and a lower portion 306b. The system 300 includes an upper layer 310 that is air, a bio layer 312, a first layer 314, and a second layer 316. In some implementations, the first 314 and second 316 layers are composed of glass. In one example, the first layer 314 is about one micrometer thick. In other examples, the first layer is less than one micrometer thick, or more than one micrometer thick. In one example, the bio layer 312 is about two micrometers thick. In other examples, the bio layer 312 is less than about two micrometers thick, or more than about two micrometers thick. In some implementations, the distance 324 between the second electrode 304 and the lower portion of the third electrode 306b is about ten micrometers. In some examples, the first 302 and second 304 electrodes, as well as the upper portion 306a and lower portion 306b of the third electrode are about two micrometers thick. In some implementations, the first 302, second 304, and upper portion 306a of the third electrodes are each about fifty (50) micrometers wide. In some examples, the distance between the first electrode 302 and the upper portion of the third electrode 306a is about ten micrometers. Similarly, in some examples, the distance between the second electrode 304 and the upper portion of the third electrode 306a is about ten micrometers. In other implementations, the electrodes can be any selected size, and various electrodes can be positioned further apart or closer together. Similarly, in various implementations, the substrate layers can be thicker or thinner than the examples included above. In various implementations, the substrates 314 and 316 are glass, and the nodes 302, 304, 306a, and 306b are gold. In other implementations, one or more of the substrates 314 and 316 are polymers. In further implementations, the nodes 302, 304, 306a, and 306b are composed of a metallic material.

Figure 4A:
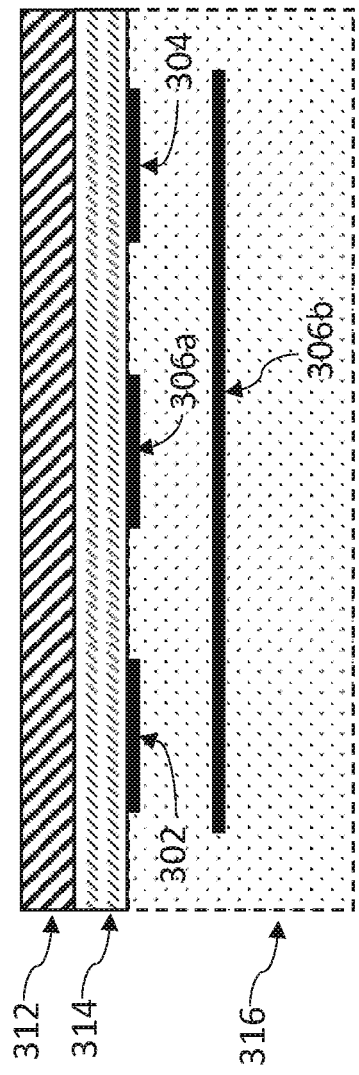
FIGS. 4A-4B illustrate impedance measurement systems for modeling, according to some embodiments of the disclosure.
Figure 4B:
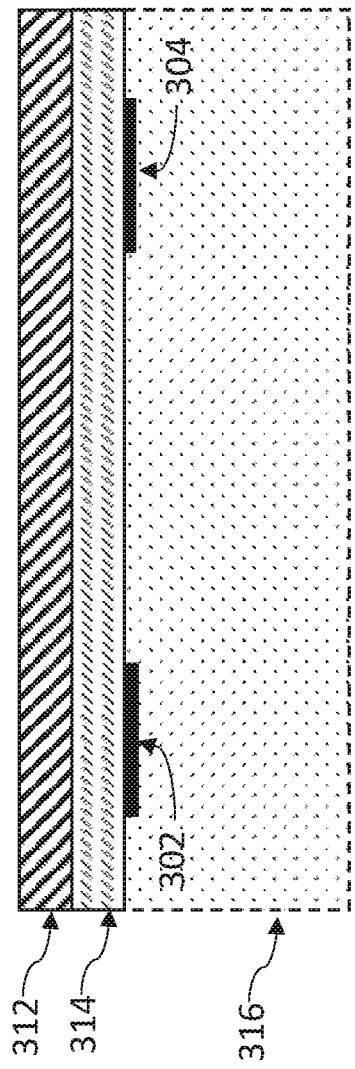

In accordance with some embodiments of the disclosure, the systems of FIGS. 4A and 4B are used to model a binding event, and illustrate the effect of the third node. To model the binding event, it is assumed that the bio layer 312 is water. The first node 302 is set to one volt, the second node 304 is set to zero volts. For the system of FIG. 4A, the gain on the third node 306 is set to one volt. The permittivity of the bio layer 312 changes from 80 to 81, and the change in the capacitance between the first 302 and second 304 nodes is measured. As shown in Table 1, as the permittivity changes from 80 to 81, the charge on the first node 302 increases from 108.01 fC to 109.26 fC, the charge on the third node 306 increases from 523.25 fC to 524.40 fC, and the charge of the second node 304 decreases from −631.27 fC to −633.66 fC. The capacitance between the first 302 and second 304 nodes increases from 108.01 fF to 109.26 fF, which is a 1.25 fF increase in capacitance, or a 1.1% capacitance change. Thus, the sensitivity of the three node device (as measured by the change in capacitance divided by the capacitance, all divided by the change in permittivity divided by the permittivity) is 0.88.

TABLE 1 measurements for FIG. 4A with the third node = 1 V

|  | $Q_1$(fC) | $C_{12}$(fF) | $Q_3$(fC) | $C_{23}$(fF) | $Q_2$(fC) |
| --- | --- | --- | --- | --- | --- |
| Permittivity($\epsilon$) 80 | 108.01 | 108.01 | 523.25 | 523.25 | −631.27 |
| Permittivity 81 | 109.26 | 109.26 | 524.40 | 524.40 | −633.66 |
| ΔC |  | 1.25 fF |  |  |  |
| ΔC/C (%) |  | 1.1% |  |  |  |
| Sensitivity (ΔC/C)/(Δε/ε) |  | 0.88 |  |  |  |

TABLE 1: measurements for FIG. 4A with the third node=1V

In contrast, for FIG. 4B, which includes only 2 electrodes, the sensitivity (as measured by the change in capacitance divided by the capacitance, all divided by the change in permittivity divided by the permittivity) is 0.54, as shown in TABLE 2. Thus, in this example, the sensitivity of the device increased by about 63% with the addition of the third electrode.

TABLE 2 measurements for FIG. 4B

|  | $Q_1$(fC) | $C_{12}$(fF) | $Q_2$(fC) |
| --- | --- | --- | --- |
| Permittivity($\epsilon$) 80 | 292.21 | 292.21 | −292.21 |
| Permittivity 81 | 294.22 | 294.22 | −294.22 |
| ΔC |  | 2.01 fF |  |
| ΔC/C (%) |  | 0.68% |  |
| Sensitivity (ΔC/C)/(Δε/ε) |  | 0.54 |  |

TABLE 2: measurements for FIG. 4B

In another example, the gain on the third node 306 in the system of FIG. 4A is set to 1.5 volts. As shown in TABLE 3, increasing the gain of the third node 306 has a controlling effect on the first node 302. For a permittivity of 80, the charge on the first node 302 changed in value from 108.01 to −153.313 with the increased gain on the third node 306. For a permittivity of 81, the charge on the first node changed in value from 109.26 to −152.650 with the increased gain on the third node 306.

TABLE 3 measurements for FIG. 4A with the third node = 1.5 V

|  | q1(fC) | q2(fC) | q3(fC) |
| --- | --- | --- | --- |
| Permittivity($\epsilon$) 80 | −153.313 | 1046.20 | −892.896 |
| Permittivity 81 | −152.650 | 1048.515 | −895.863 |

TABLE 3: measurements for FIG. 4A with the third node=1.5V

Thus, the gain on the third node 306 can be optimized for maximum sensitivity of the permittivity at the binding elements.

Figure 5B:
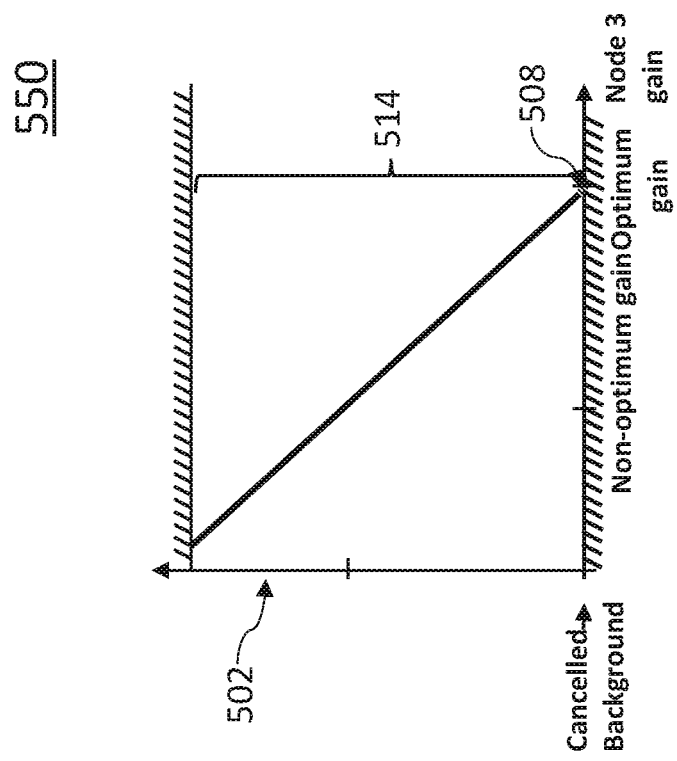
FIGS. 5A and 5I are graphs that illustrate properties of an impedance measurement system, according to some embodiments of the disclosure.
Figure 5A:
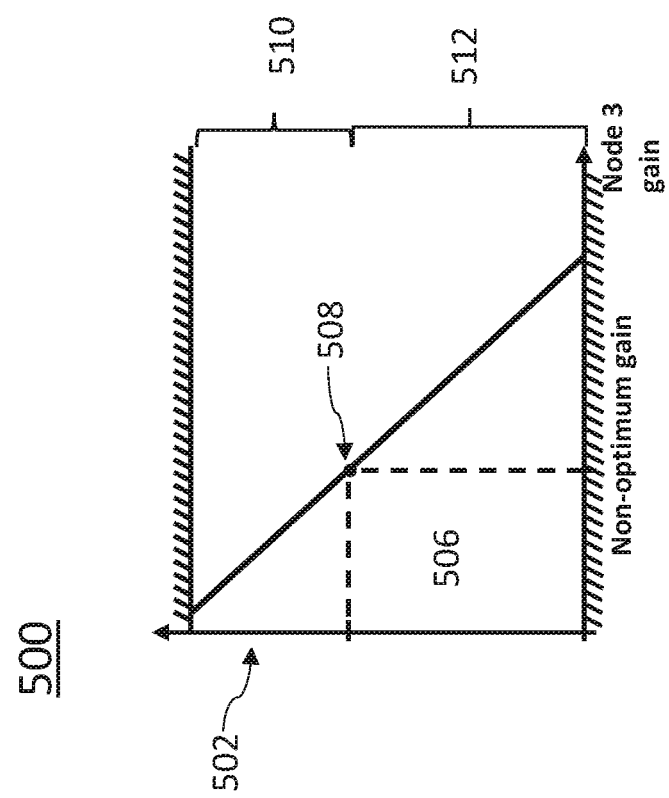

FIGS. 5A and 5B plot the node 1 capacitance (or AC current, or charge) against the node 3 gain for an impedance measurement system such as that shown in FIGS. 2A, 3 and 4A. FIG. 5A shows the graph for a non-optimized gain case. FIG. 5B shows the graph for an optimized gain case. The vertical axis 502 is the capacitance on the first node. The top of each graph is marked by the dynamic range limit, or the maximum capacitance that can be measured which, in one example, is determined by the dynamic range of the measurement system. In a single supply system, as shown in FIGS. 5A and 5B, the x-axis, the bottom line of the plots, is also a limit on the dynamic range.

Referring to FIG. 5A, the background capacitance 506 is wasted measurement dynamic range. The operating point 508 is just above the dotted line, and the change between the background capacitance 506 and the maximum capacitance is the usable dynamic range 510 of the system. Since the operating point 508 is in the middle of the capacitance range, much of the dynamic range is wasted background range 512.

In FIG. 5B, the gain is optimized, and the background capacitance is essentially zero, so there is much larger useable dynamic range 514. The operating point 508 is approximately zero. The slope of the gain of the system can be changed to yield a much higher signal output for a given signal input.

Figure 6:
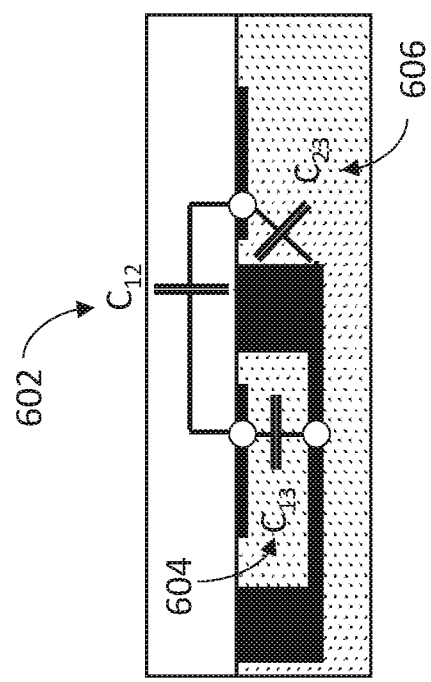
FIG. 6 is a model of an impedance measurement system and showing the capacitances between the three nodes of the system, according to some embodiments of the disclosure.

FIG. 6 shows a model of an impedance measurement system 600 illustrating the capacitances between the three nodes of the system, according to various embodiments of the disclosure. The first $C_{12}$ capacitance 602 is the capacitance between the first node and the second node. The second $C_{13}$ capacitance 604 is the capacitance between the first node and the third node. The third $C_{23}$ capacitance 606 is the capacitance between the second node and the third node. Similarly, $V_1$ is the voltage at the first node, $V_2$ is the voltage at the second node, and $V_3$ is the voltage at the third node. At the optimum operating point, the charge $Q_1$ on the first node is minimized. The optimum gain is set by the physical size of the structure, and the properties of the materials involved. The optimum gain relates to the ratio of $C_{12}$ to $C_{13}$. In particular, if $V_2$ is equal to ground, then $Q_1=V_1 C_{12}+(V_1-V_3)C_{13}$. For an optimized gain, then $Q_1=V_1C_{12}+(V_1-V_3)C_{13}=0$. Thus:

$$V_3/V_1 = 1 + C_{12}/C_{13} \quad (1)$$

Using Equation 1, the gain on the third electrode ($V_3$) can be set to optimize the impedance measurement system.

Figure 7A:
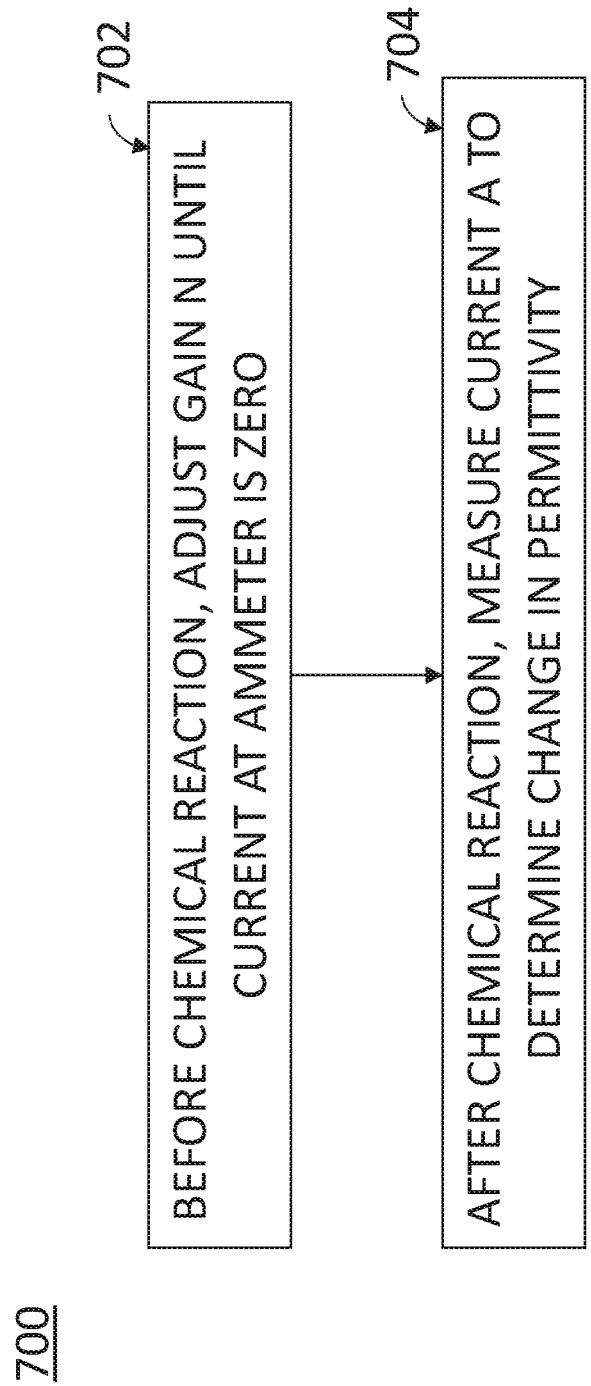
FIGS. 7A and 7B show two methods for optimizing gain to determine permittivity, according to some embodiments of the disclosure.
Figure 7B:
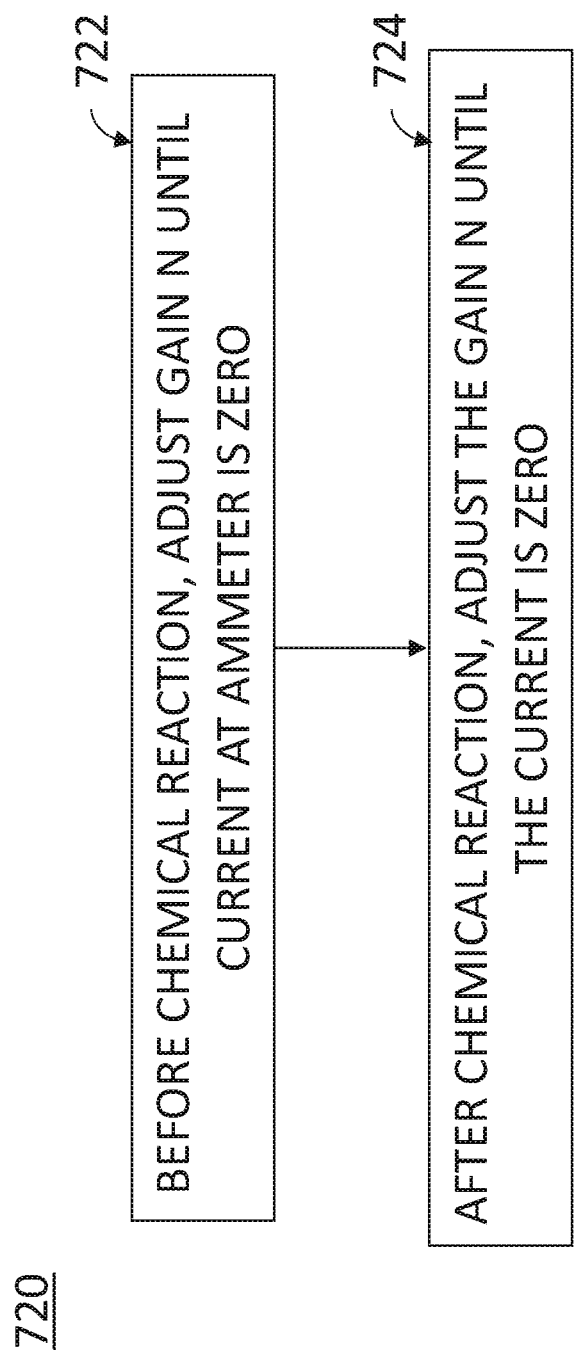

In particular, FIGS. 7A and 7B show two methods for optimizing the gain to determine the permittivity. Referring to FIG. 7A, at step 702 before the chemical reaction begins (before the analyte is introduced), the gain N is adjusted until the current at the ammeter is zero, indicating no charge on the first node. Thus, the initial conditions are set up before the binding event occurs. Note that the impedance measurement system can be used in many different environments, and so the gain N is adjusted Just prior to the chemical reaction. For example, if the temperature changes, the properties of the materials change and the optimum setting changes. After the initial conditions are set at step 702, the binding events are introduced. At step 704, after the chemical reaction, the change in the current A at the ammeter is used to determine the permittivity.

In FIG. 7B, at step 722 before the chemical reaction begins (before the analyte is introduced), the gain N is adjusted until the current at the ammeter is zero, indicating no charge on the first node. After the chemical reaction, at step 724, the gain N is again adjusted until the ammeter measures zero current, and the change in the gain indicates the permittivity.

Because the impedance measurement system is dynamic, it is robust. In particular, the system can be initialized each time it is used to adjust to the optimal point, and thus is accurate regardless of changes in temperature, environment, or materials.

Figure 1:
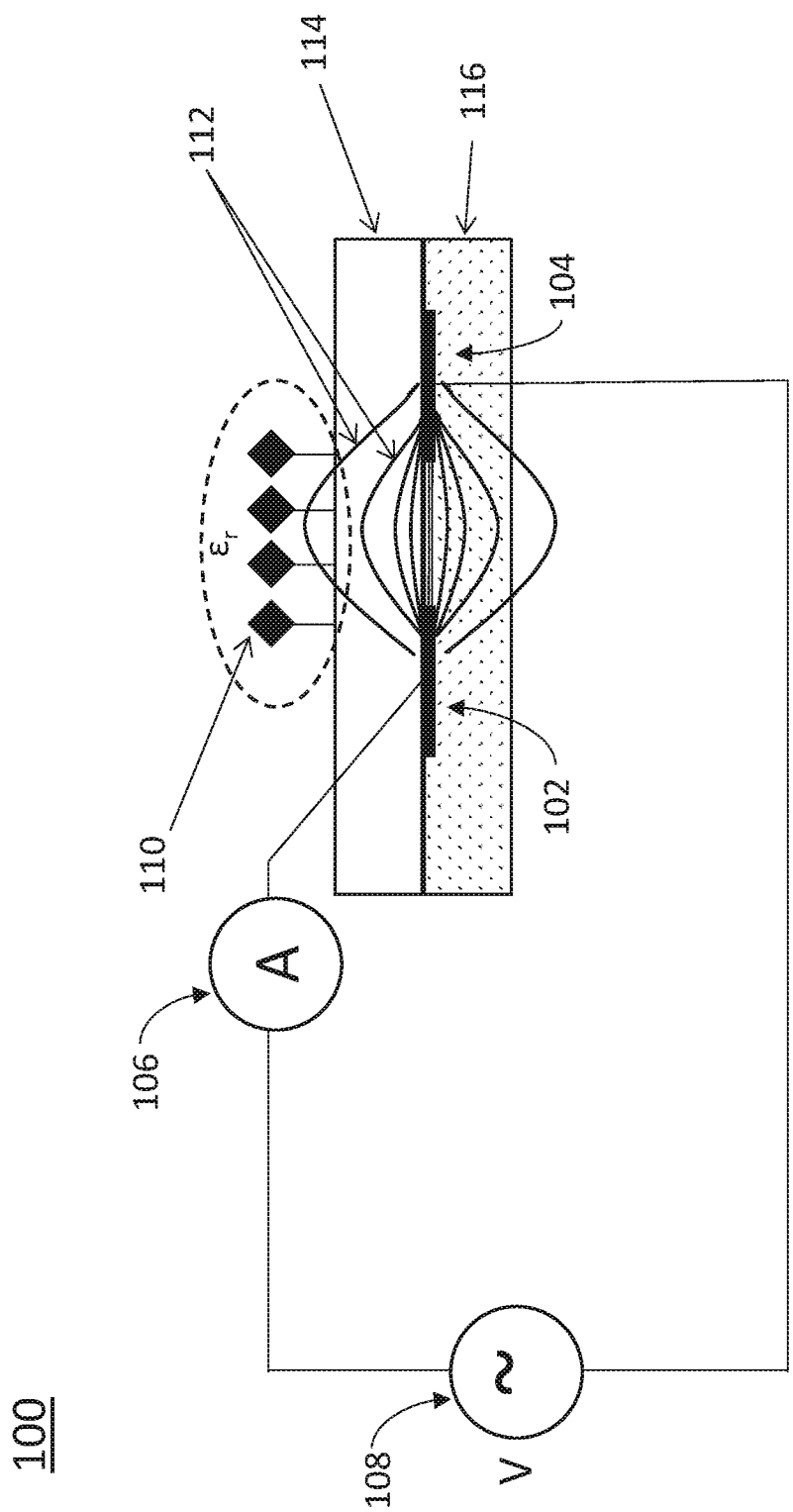
FIG. 1 is a diagram illustrating an impedance measurement system.
Figure 8B:
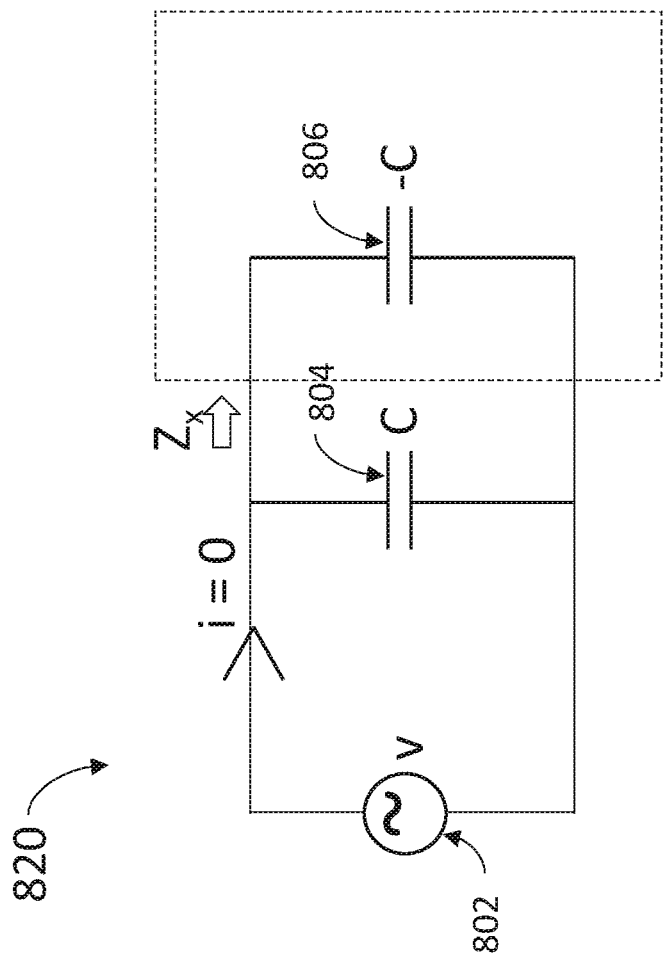
FIG. 8B illustrates a circuit model of an impedance measurement system, according to some embodiments of the disclosure.
Figure 8A:
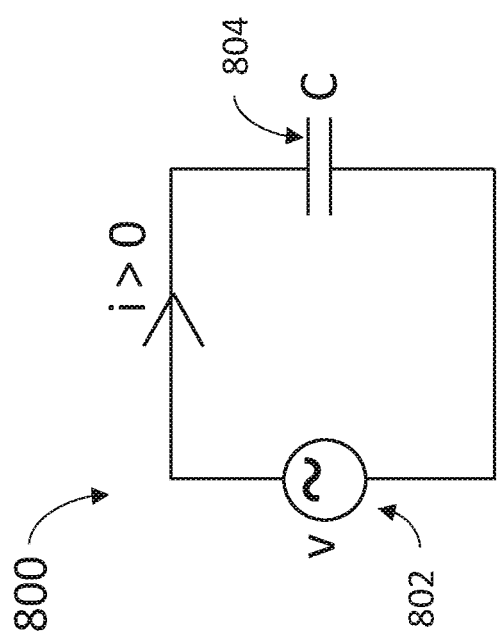
FIG. 8A illustrates a circuit model of an impedance measurement system.

FIG. 8B illustrates a circuit model of the impedance measurement system of FIG. 2A. FIG. 8A illustrates a circuit model of the impedance measurement system of FIG. 1, and includes a capacitor in which voltage is applied, resulting in a non-zero current. In FIG. 8B, by adjusting the current to zero, the resulting circuit model effectively includes a negative capacitor in parallel with the positive capacitor. With the negative capacitor in parallel with the positive capacitor, the capacitances are summed, allowing for a current of zero.

Figure 9B:
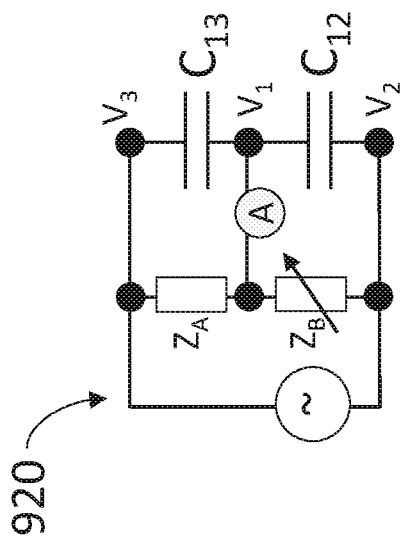
FIGS. 9A-9D show circuit implementations of an impedance measurement system, according to some embodiments of the disclosure.
Figure 9D:
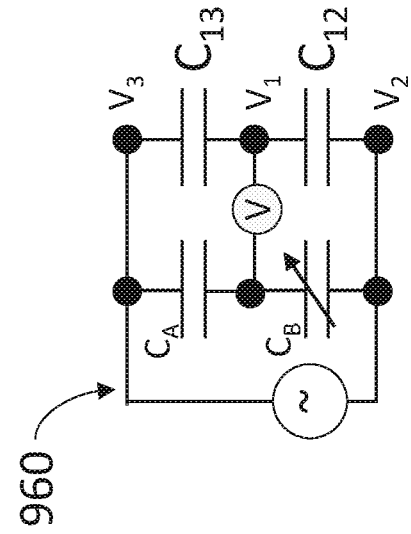
Figure 9A:
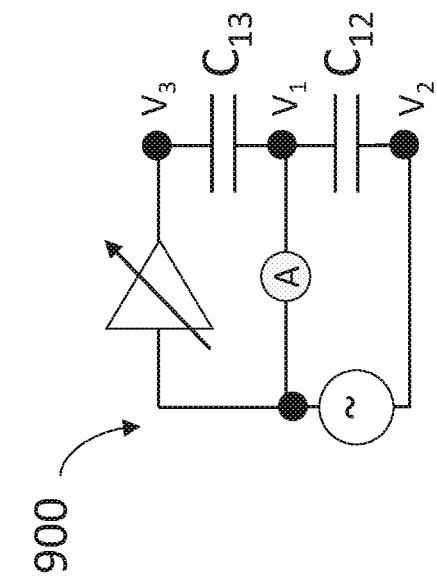

FIGS. 9A-9D show several alternative circuit implementations of the system of FIG. 2A. FIG. 9A shows a gain circuit 900 with the voltage source connected to the ammeter to node $V_1$. Node $V_2$ is equal to ground, and node $V_3$ is connected to the gain. Thus, as shown in FIG. 9A, the system can be modeled as if it included just two capacitors: $C_{13}$ and $C_{12}$. When a voltage is applied, there is a gain stage, and the current is measured at the ammeter.

FIG. 9B shows a circuit 920, including impedance elements which implement attenuation. The attenuation is included in place of the gain of FIG. 9A, and achieves the same effect. In particular, an AC voltage is applied across the stack of capacitors $C_{12}$ and $C_{13}$, and an impedance divider, in parallel with the capacitors, implements the gain. The first impedance $Z_A$ is constant and the second impedance $Z_B$ is a variable impedance. In particular, since at optimization, assuming $V_2$ is zero, the current at the ammeter equals zero:

$$V_1 = (V_3 Z_B)/(Z_A + Z_B) \quad (2)$$

and the gain is $V_3/V_1$, where $$V_3/V_1 = 1 + Z_A/Z_B \quad (3)$$

Thus, optimization occurs when:

$$Z_B/(Z_A + Z_B) = C_{13}/(C_{12} + C_{13}) \quad (4)$$

According to some implementations, using impedances in place of the amplifier decreases the noise of the system, since amplifiers generally introduce significantly more noise to a system than impedances.

Figure 9C:
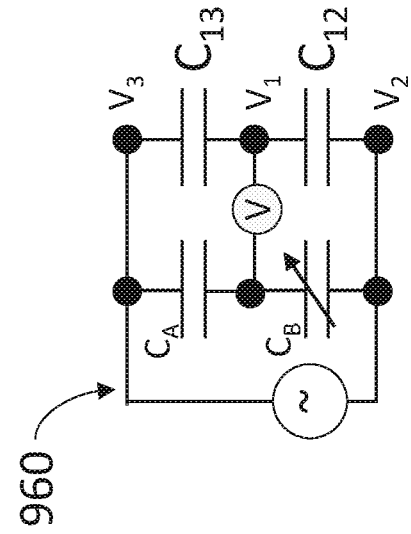

As shown in the circuit 940 in FIG. 9C, the impedance can be implemented using two resistors, a first constant resistor $R_A$ and a second variable resistor $R_B$. In some implementations, an RDAC (Resistive Digital to Analog Converter) is used to produce the variable resistor impedance ratio. (Also shown in FIG. 9C, a voltmeter can be used in place of the ammeter. The voltmeter can be used because the current is zero at optimization, and a zero measurement at an ammeter is equivalent to a zero measurement at a voltmeter. Thus, at optimum gain, the voltage is zero.

FIG. 9D shows a circuit 960, in which the impedance of FIG. 9B is implemented using two CAPDACs (Capacitive Digital to Analog Converters), a first constant CAPDAC $C_A$ and a second variable CAPDAC $C_B$. In other implementations, the impedances of FIG. 9D are implemented using a combination of resistors and capacitors.

FIGS. 10A and 10B show a layout for an impedance measurement system, according to some embodiments of the disclosure. FIG. 10A shows an elevation view 1000 of an impedance measurement system design. As shown in FIG. 10A, the third node 1006 forms a well around node 1002.

In one implementation, FIG. 10B shows a plan view 1020 of the layout of FIG. 10A, and the layout in the elevation view 1000 of FIG. 10A is a cross-section of the circular layout shown in FIG. 10B. In the circular layout, the third node 1006 has a well-shape including a descended bottom element, parallel to the first 1002 and second 1004 nodes, and a wide circular side around the bottom element, extending up to the positions of the first 1002 and second 1004 nodes. As shown in the layout in FIG. 10A and in the plan view of FIG. 10B, the first node 1002 is positioned in the center of the circle, surrounded by the side wall of the third node 1006, and first 1002 and third 1006 nodes are both surrounded by the second node 1004, which is also circular and has a hollow center.

In one aspect, the layout is designed to maximize the area containing binding events to improve transduction. In some implementations, the pattern is repeated with additional circular electrode elements surrounding the first 1004, third 1006, and second 1004 nodes shown in FIGS. 10A and 10B.

In some implementations, the layout shown in FIG. 10A is an elevation view of an elongated impedance measurement system design having straight electrodes positioned in parallel to one another.

In some implementations, the third node 1006 is implemented as two separate electrodes (one on level with the first and second electrodes, and one positioned underneath the other electrodes). In various implementations, the two electrodes of the third node are set to the same voltage.

In various implementations, the area containing binding events is maximized to improve transduction.

Figure 10D:
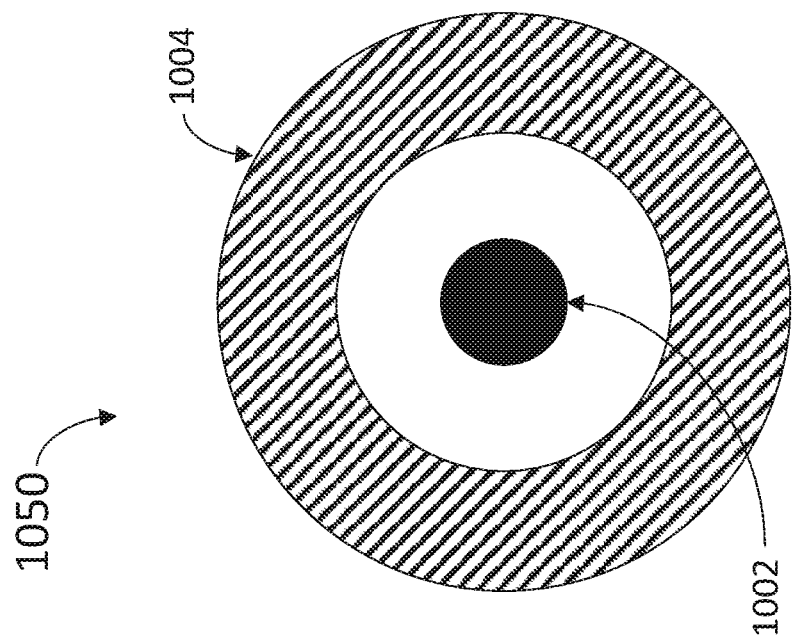
Figure 10C:
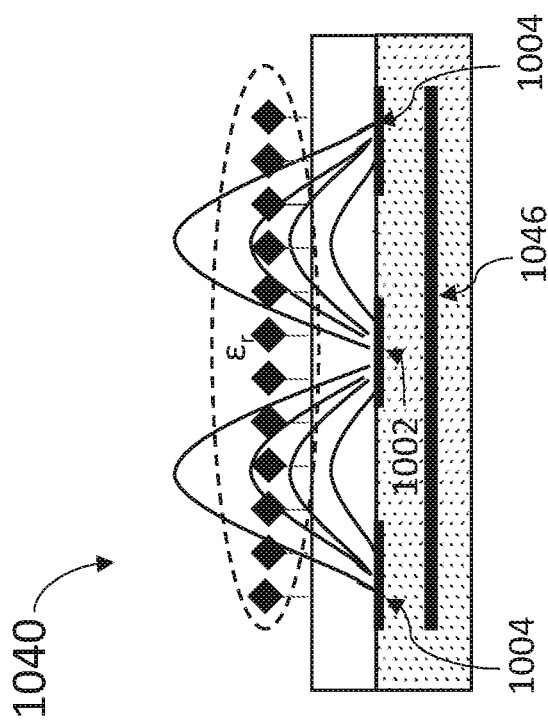

FIGS. 10C and 10D show a layout for an impedance measurement system, according to some embodiments of the disclosure. FIG. 10C shows an elevation view 1040 of an impedance measurement system design. As shown in FIG. 10C, the third node 1046 is positioned below nodes 1002 and 1004.

In one implementation, FIG. 10D shows a plan view 1050 of the layout of FIG. 10C, and the layout shown in the elevation view 1040 of FIG. 10C is a cross-section of the circular layout shown in FIG. 10D. In the circular layout, the third node 1046 is a descended bottom element, parallel to the first 1002 and second 1004 nodes. As shown in the layout in FIG. 10C and in the plan view of FIG. 10D, the first node 1002 is positioned in the center of the circle, and first 1002 node is surrounded by the second node 1004, which is also circular and has a hollow center. The third node 1046 is positioned below and parallel to the first 1002 and second 1004 nodes.

In one aspect, the layout is designed to maximize the area containing binding events to improve transduction. In some implementations, the pattern is repeated with additional circular electrode elements surrounding the first 1004 and second 1004 nodes shown in FIGS. 10C and 10D.

In some implementations, the layout shown in FIG. 10C is an elevation view of an elongated impedance measurement system design having straight electrodes positioned in parallel to one another.

Figure 11:
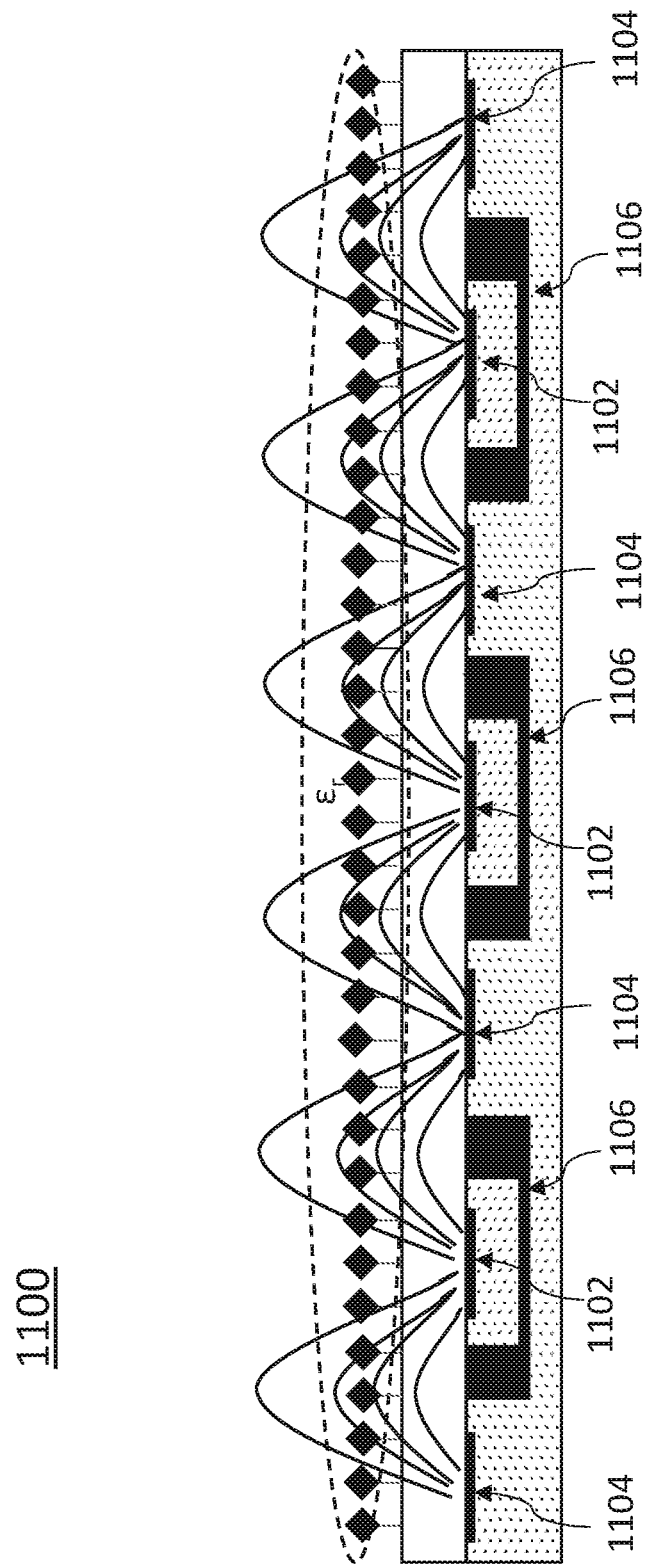
FIG. 11 shows a layout for an impedance measurement system, according to some embodiments of the disclosure.

FIG. 11 shows another alternative elevation view 1100 of an impedance measurement system, according to some embodiments of the disclosure. The elevation view of FIG. 11 includes multiple first 1102, second 1104, and third 1106 electrodes in a repeating pattern. According to various embodiments, the impedance measurement system discussed herein can be implemented in an interdigitated pattern including any number of electrodes.

Figure 12:
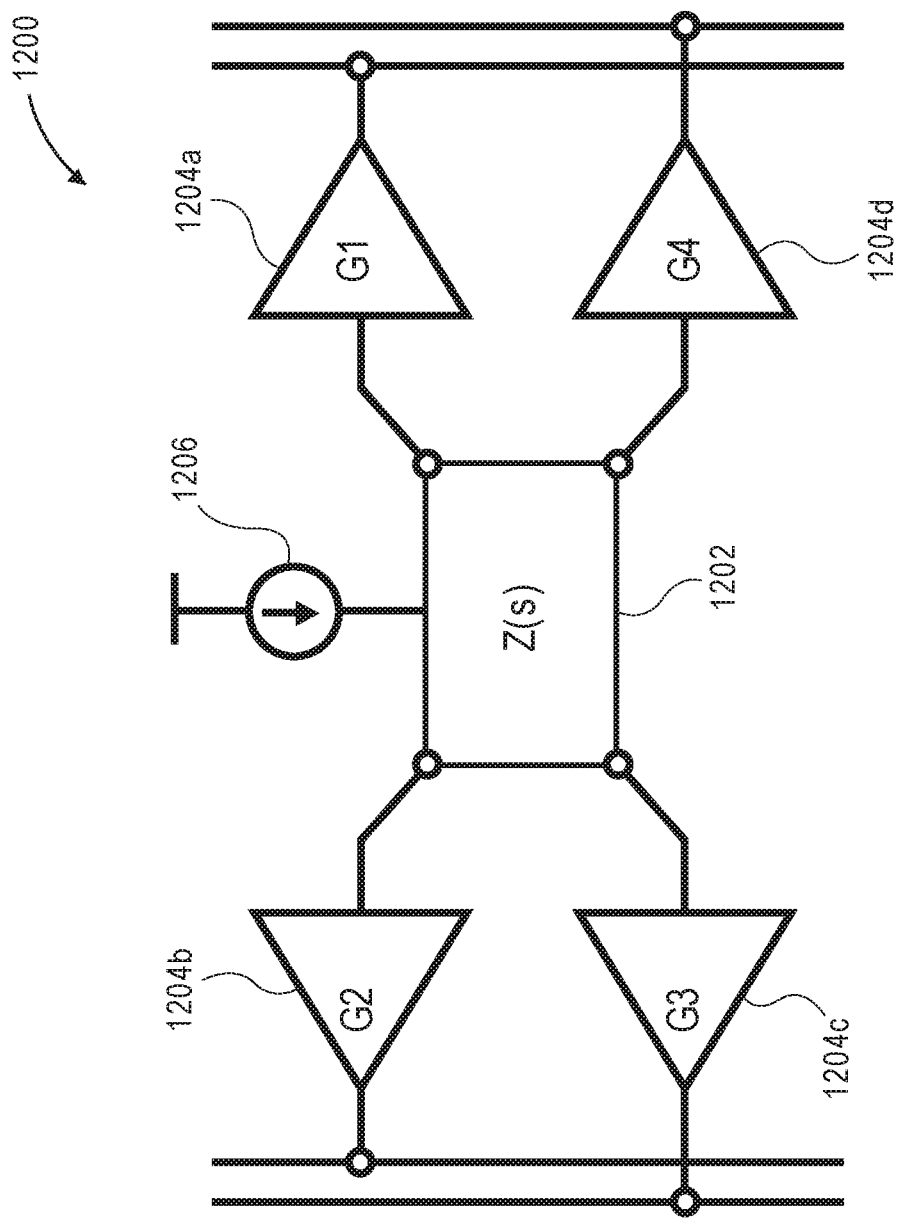
FIG. 12 shows an impedance measurement system connected to several amplifiers, according to some embodiments of the disclosure.

FIG. 12 shows an impedance measurement system 1200 including an impedance measurement sensor cell 1202 connected to amplifiers 1204a-1204d and an input 1206, according to some embodiments of the disclosure. In some implementations, an impedance measurement sensor system includes multiple impedance measurement sensor cells 1202, as shown in the impedance measurement system 1300 of FIG. 13.

Figure 13:
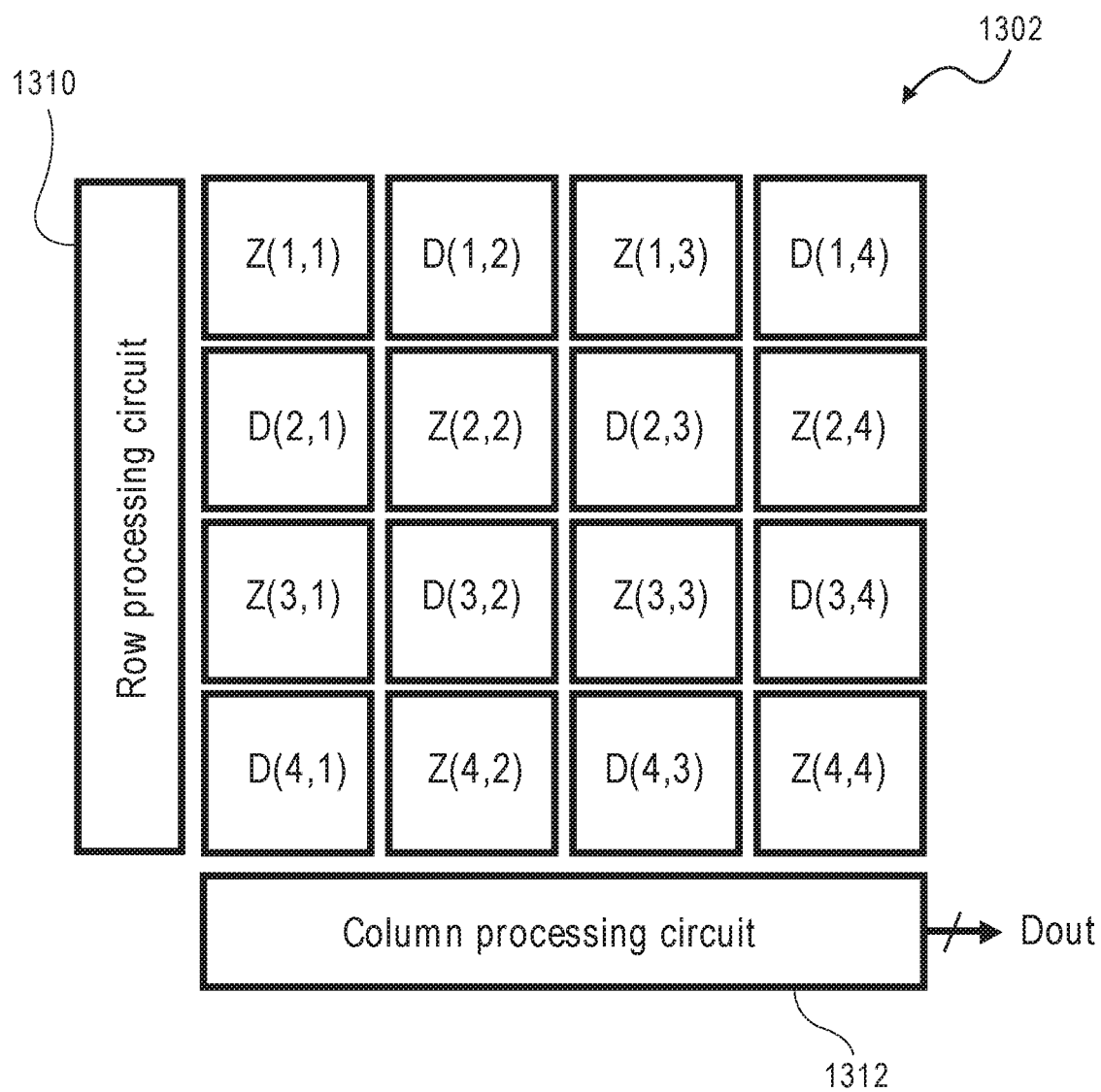
FIG. 13 shows an impedance measurement system including a 2-dimensional matrix of cells, according to some embodiments of the disclosure.

FIG. 13 shows an impedance measurement system 1300 including a 2-dimensional matrix of cells 1302, according to some embodiments of the disclosure. In some implementations, the matrix of cells 1302 monitors chemical reactions between cells and in the overall impedance measurement system 1300. In other implementations, the impedance measurement system 1300 is used for single cell excitation and detection with multiplexors and signal lines.

Each cell in the matrix of cells 1302 is an impedance measurement sensor and has an input and output. The impedance measurement system 1300 includes a row processing circuit 1310 and a column processing circuit 1312. In one implementation, the row processing circuit 1310 provides an input signal to one or more of the cells in the matrix of cells 1302, and the column processing circuit 1312 receives the output signal from one of more the cells in the matrix of cells 1302. The column processing circuit 1312 outputs the output signal $D_{out}$. The row processing circuit 1310 includes one or more multiplexors. Similarly, the column processing circuit 1312 includes one or more multiplexors.

According to one implementation, one or more of the cells in the matrix of cells 1302 receives an input signal from the row processing circuit 1310 and outputs an output signal to the column processing circuit 1312. In some implementations, one or more of the cells in the matrix of cells 1302 senses an input signal, and one or more of the cells in the matrix of cells 1302 is driven by an input signal from the row processing circuit 1310. In some implementations, the cells labeled Z(n,m) are activated by an input signal from the row processing circuit 1310, and the neighbor cells labeled D(n,m) are scanning cells. In one example, one cell is activated, and the output is gathered from one or more neighboring cells. For example, the cell labeled Z(2,2) is activated, and output is used from one or more of the neighboring cells labeled D(1,2), D(2,1), D2,3), and D(3,2). In other examples, multiple cells are activated, and output is gathered from one or more cells neighboring any of the activated cells. In further examples, multiple cells are activated, and output is gathered from one cell neighboring any of the activated cells. In some implementations, one or more cells from a selected row of the matrix of cells 1302 is activated, and output is sensed from one or more cells from a selected column of the matrix of cells 1302.

In some implementations, each cell in the matrix of cells 1302 includes an impedance measurement system 200 as shown in FIG. 2A. In some implementations, each cell in the matrix of cells 1302 includes connections to the three signals lines shown in FIG. 2A, the lines coupled to the first 202, second 204, and third 206 nodes. The signals appear at one or more of the cells in the matrix of cells 1302 when a row decode is activated. In one example, the output line from the second node 204 is output to the column processing circuit 1312. In some implementations, multiple cells from a matrix of cells 1302 share one or more amplifiers as shown in greater detail in FIG. 12.

FIG. 12 shows a system with a single sensor cell 1202 connected to first 1204a second 1204b, third 1204c, and fourth 1204d amplifiers. A signal is input to the sensor cell 1202 at input 1206. In some examples, the input signal is a voltage, resulting in an output current, as described in greater detail above with respect to FIG. 2A. In FIG. 12, one or more of the first 1204a second 1204b, third 1204c, and fourth 1204d amplifiers amplifies the output signal.

According to various implementations, the amplifiers 1204a-1204d shown in FIG. 12 are used with the sensor cells in the matrix of cells 1302 of FIG. 13. In particular, in some implementations, an output line from one or more of the cells in the matrix of cells 1302 is connected to one or more amplifiers, and the output from the one or more amplifiers is connected to the column processing circuit 1312. In one example, output from the cells in the matrix of cells 1302 is amplified, and the amplified output is received by the column processing circuit 1312. In some examples, each cell of the matrix of cells 1302 is connected to multiple amplifiers. In some examples, multiple cells from the matrix of cells 1302 share one or more amplifiers.

Referring back to FIG. 12, in some implementations, the output current is converted to an output voltage. In some implementations, the impedance measurement system 1200 includes a ground (not shown), and a DC electrode input line. In some implementations the impedance measurement system 1200 includes three driving nodes. In various examples, the impedance measurement system 1200 includes the same inputs as those shown in FIG. 2.

Figure 14:
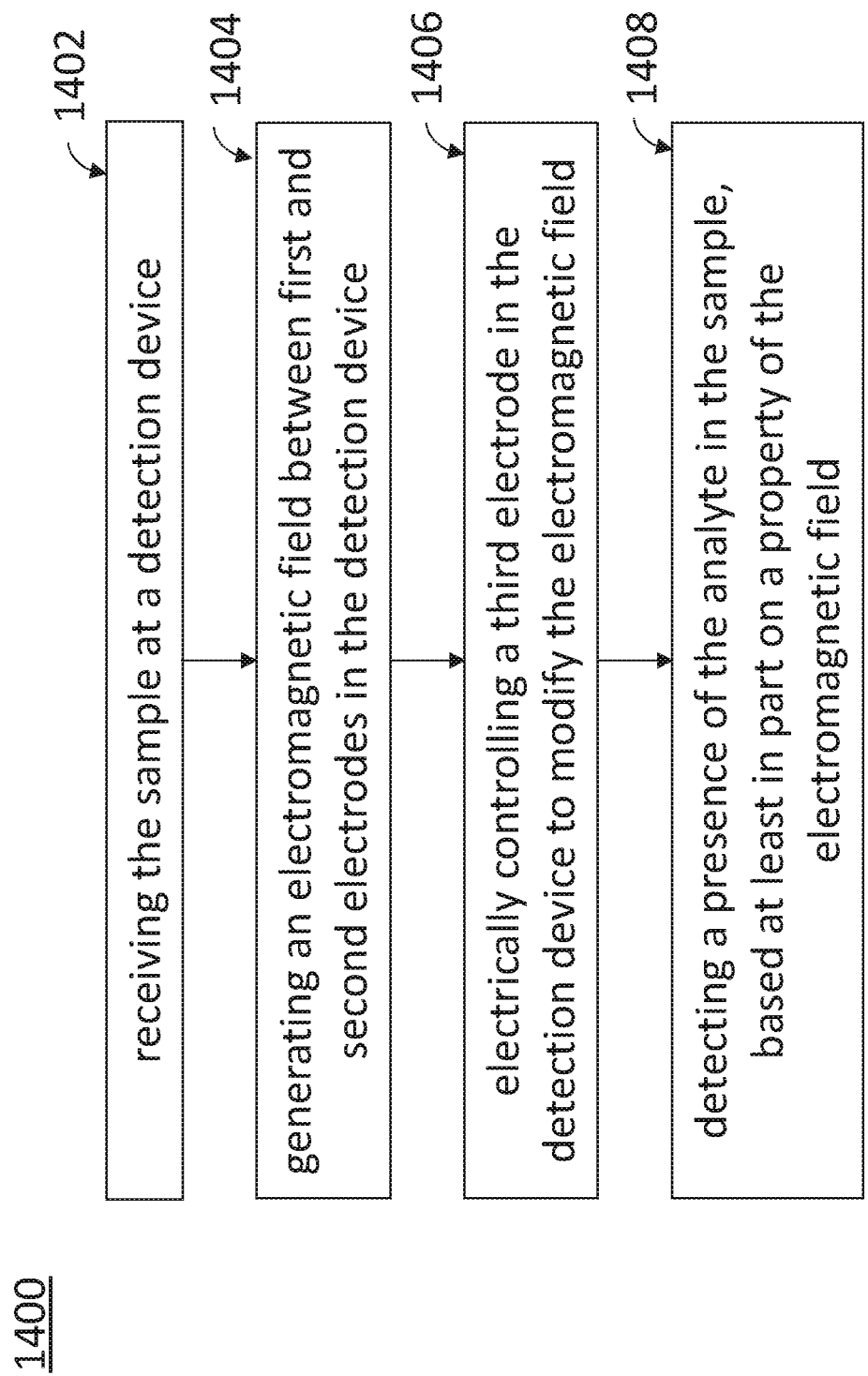
FIG. 14 shows a flow chart of a method for detecting an analyte in a sample using impedance measurements, according to some embodiments of the disclosure.

FIG. 14 is a flow chart of a method 1400 for detecting an analyte in a sample using impedance measurements, according to some embodiments of the disclosure. At step 1402, a sample is received at the detection device. At step 1404, an electromagnetic field is generated between first and second electrodes in the detection device. At step 1406, a third electrode in the detection device is electrically controlled to modify the electromagnetic field. At step 1408, a presence of the analyte in the sample is detected, based at least in part on a property of the electromagnetic field.

Variations and Implementations

In the discussions of the embodiments above, the capacitors, clocks, DFFs, dividers, inductors, resistors, amplifiers, switches, digital core, transistors, and/or other components can readily be replaced, substituted, or otherwise modified in order to accommodate particular circuitry needs. Moreover, it should be noted that the use of complementary electronic devices, hardware, software, etc. offer an equally viable option for implementing the teachings of the present disclosure.

In one example embodiment, any number of electrical circuits of the FIGS. may be implemented on a board of an associated electronic device. The board can be a general circuit board that can hold various components of the internal electronic system of the electronic device and, further, provide connectors for other peripherals. More specifically, the board can provide the electrical connections by which the other components of the system can communicate electrically. Any suitable processors (inclusive of digital signal processors, microprocessors, supporting chipsets, etc.), computer-readable non-transitory memory elements, etc. can be suitably coupled to the board based on particular configuration needs, processing demands, computer designs, etc. Other components such as external storage, additional sensors, controllers for audio/video display, and peripheral devices may be attached to the board as plug-in cards, via cables, or integrated into the board itself. In various embodiments, the functionalities described herein may be implemented in emulation form as software or firmware running within one or more configurable (e.g., programmable) elements arranged in a structure that supports these functions. The software or firmware providing the emulation may be provided on non-transitory computer-readable storage medium comprising instructions to allow a processor to carry out those functionalities.

In another example embodiment, the electrical circuits of the FIGURES may be implemented as stand-alone modules (e.g., a device with associated components and circuitry configured to perform a specific application or function) or implemented as plug-in modules into application specific hardware of electronic devices. Note that particular embodiments of the present disclosure may be readily included in a system on chip (SOC) package, either in part, or in whole. An SOC represents an IC that integrates components of a computer or other electronic system into a single chip. It may contain digital, analog, mixed-signal, and often radio frequency functions: all of which may be provided on a single chip substrate. Other embodiments may include a multi-chip-module (MCM), with a plurality of separate ICs located within a single electronic package and configured to interact closely with each other through the electronic package. In various other embodiments, the clocking and filtering functionalities may be implemented in one or more silicon cores in Application Specific Integrated Circuits (ASICs), Field Programmable Gate Arrays (FPGAs), and other semiconductor chips.

It is also imperative to note that all of the specifications, dimensions, and relationships outlined herein (e.g., the number of processors, logic operations, etc.) have only been offered for purposes of example and teaching only. Such information may be varied considerably without departing from the spirit of the present disclosure, or the scope of the appended claims. The specifications apply only to one non-limiting example and, accordingly, they should be construed as such. In the foregoing description, example embodiments have been described with reference to particular processor and/or component arrangements. Various modifications and changes may be made to such embodiments without departing from the scope of the appended claims. The description and drawings are, accordingly, to be regarded in an illustrative rather than in a restrictive sense.

Note that the activities discussed above with reference to the FIGURES are applicable to any integrated circuits that involve signal processing, particularly those that use sampled analog, some of which may be associated with processing real-time data. Certain embodiments can relate to multi-DSP signal processing, floating point processing, signal/control processing, fixed-function processing, microcontroller applications, etc.

In certain contexts, the features discussed herein can be applicable to medical systems, scientific instrumentation, wireless and wired communications, radar, industrial process control, audio and video equipment, current sensing, instrumentation (which can be highly precise), and other digital-processing-based systems.

Moreover, certain embodiments discussed above can be provisioned in digital signal processing technologies for medical imaging, patient monitoring, medical instrumentation, and home healthcare. This could include pulmonary monitors, accelerometers, heart rate monitors, pacemakers, etc. Other applications can involve automotive technologies for safety systems (e.g., stability control systems, driver assistance systems, braking systems, infotainment and interior applications of any kind). Furthermore, powertrain systems (for example, in hybrid and electric vehicles) can use high-precision data conversion products in battery monitoring, control systems, reporting controls, maintenance activities, etc.

In yet other example scenarios, the teachings of the present disclosure can be applicable in the industrial markets that include process control systems that help drive productivity, energy efficiency, and reliability. In consumer applications, the teachings of the signal processing circuits discussed above can be used for image processing, auto focus, and image stabilization (e.g., for digital still cameras, camcorders, etc.). Other consumer applications can include audio and video processors for home theater systems, DVD recorders, and high-definition televisions. Yet other consumer applications can involve advanced touch screen controllers (e.g., for any type of portable media device). Hence, such technologies could readily part of smartphones, tablets, security systems, PCs, gaming technologies, virtual reality, simulation training, etc.

Note that with the numerous examples provided herein, interaction may be described in terms of two, three, four, or more electrical components. However, this has been done for purposes of clarity and example only. It should be appreciated that the system can be consolidated in any suitable manner. Along similar design alternatives, any of the illustrated components, modules, and elements of the FIGURES may be combined in various possible configurations, all of which are clearly within the broad scope of this Specification. In certain cases, it may be easier to describe one or more of the functionalities of a given set of flows by only referencing a limited number of electrical elements. It should be appreciated that the electrical circuits of the FIGURES and its teachings are readily scalable and can accommodate a large number of components, as well as more complicated/sophisticated arrangements and configurations. Accordingly, the examples provided should not limit the scope or inhibit the broad teachings of the electrical circuits as potentially applied to a myriad of other architectures.

Note that in this Specification, references to various features (e.g., elements, structures, modules, components, steps, operations, characteristics, etc.) included in "one embodiment", "example embodiment", "an embodiment", "another embodiment", "some embodiments", "various embodiments", "other embodiments", "alternative embodiment", and the like are intended to mean that any such features are included in one or more embodiments of the present disclosure, but may or may not necessarily be combined in the same embodiments.

It is also important to note that the functions related to clocking in sampled analog systems, illustrate only some of the possible clocking functions that may be executed by, or within, systems illustrated in the FIGURES. Some of these operations may be deleted or removed where appropriate, or these operations may be modified or changed considerably without departing from the scope of the present disclosure. In addition, the timing of these operations may be altered considerably. The preceding operational flows have been offered for purposes of example and discussion. Substantial flexibility is provided by embodiments described herein in that any suitable arrangements, chronologies, configurations, and timing mechanisms may be provided without departing from the teachings of the present disclosure.

Numerous other changes, substitutions, variations, alterations, and modifications may be ascertained to one skilled in the art and it is intended that the present disclosure encompass all such changes, substitutions, variations, alterations, and modifications as falling within the scope of the appended claims. In order to assist the United States Patent and Trademark Office (USPTO) and, additionally, any readers of any patent issued on this application in interpreting the claims appended hereto, Applicant wishes to note that the Applicant: (a) does not intend any of the appended claims to invoke paragraph six (6) of 35 U.S.C. section 112 as it exists on the date of the filing hereof unless the words "means for" or "step for" are specifically used in the particular claims; and (b) does not intend, by any statement in the specification, to limit this disclosure in any way that is not otherwise reflected in the appended claims.

OTHER NOTES, EXAMPLES, AND IMPLEMENTATIONS

Note that all optional features of the apparatus described above may also be implemented with respect to the method or process described herein and specifics in the examples may be used anywhere in one or more embodiments.

In a first example, a system is provided (that can include any suitable circuitry, dividers, capacitors, resistors, inductors, ADCs, DFFs, logic gates, software, hardware, links, etc.) that can be part of any type of computer, which can further include a circuit board coupled to a plurality of electronic components. The system can include means for clocking data from the digital core onto a first data output of a macro using a first clock, the first clock being a macro clock; means for clocking the data from the first data output of the macro into the physical interface using a second clock, the second clock being a physical interface clock; means for clocking a first reset signal from the digital core onto a reset output of the macro using the macro clock, the first reset signal output used as a second reset signal; means for sampling the second reset signal using a third clock, which provides a clock rate greater than the rate of the second clock, to generate a sampled reset signal; and means for resetting the second clock to a predetermined state in the physical interface in response to a transition of the sampled reset signal.

The 'means for' in these instances (above) can include (but is not limited to) using any suitable component discussed herein, along with any suitable software, circuitry, hub, computer code, logic, algorithms, hardware, controller, interface, link, bus, communication pathway, etc. In a second example, the system includes memory that further comprises machine-readable instructions that when executed cause the system to perform any of the activities discussed above.

What is claimed is:

1. An impedance measurement system to detect an analyte in a sample, comprising:
    first, second, and third electrodes, wherein at least a portion of the third electrode is positioned between the first and second electrodes, wherein the first electrode has a first potential, the second electrode has a second potential, and the third electrode has a third potential, and wherein the first, second, and third potentials are each different;
    means for generating an electromagnetic field between the first and second electrodes;
    means for electrically controlling the third electrode, wherein the third electrode modifies the electromagnetic field, steering electric field lines between the first and second electrodes upwards; and
    a processor for detecting a presence of the analyte in the sample, based at least in part on a property of the electromagnetic field.

2. The impedance measurement system of claim 1, wherein the processor is further configured to measure a property of the analyte.

3. The impedance measurement system of claim 1, wherein the means for generating an electromagnetic field between the first and second electrodes is one of a voltage source and a current source.

4. The impedance measurement system of claim 1, further comprising an ammeter for measuring a current on the first electrode, wherein the processor detects the presence of the analyte based in part on the current measurement, and wherein the means for electrically controlling the third electrode adjusts a gain of the third electrode based at least in part on the current measurement.

5. The impedance measurement system of claim 1, wherein the means for electrically controlling the third electrode is one of an amplifier and an impedance device.

6. The impedance measurement system of claim 5, wherein the impedance device is at least one of a resistor and a capacitor.

7. The impedance measurement system of claim 6, wherein the impedance device includes one of a resistive digital-to-analog converter and a capacitive digital-to-analog converter.

8. The impedance measurement system of claim 1, further comprising a voltmeter for measuring a voltage at the first electrode, wherein the processor detects the presence of the analyte based in part on the voltage measurement.

9. The impedance measurement system of claim 8, wherein the means for electrically controlling the third electrode adjusts a gain of the third electrode based at least in part on the voltage measurement.

10. An impedance measurement system to detect an analyte in a sample, comprising:
    first, second, and third electrodes, wherein at least a portion of the third electrode is positioned between the first and second electrodes, wherein the first electrode has a first potential, the second electrode has a second potential, and the third electrode has a third potential, and wherein the first, second, and third potentials are each different;
    a voltage source, coupled to the first electrode, wherein the voltage source generates an electromagnetic field between the first and second electrodes;
    a circuit element configured to adjust a gain at the third electrode, wherein the gain at the third electrode modifies the electromagnetic field, steering the electromagnetic field between the first and second electrodes upwards; and
    a processor for detecting a presence of the analyte in the sample, based at least in part on a property of the electromagnetic field.

11. The impedance measurement system of claim 10, wherein the processor is further configured to measure a property of the analyte.

12. The impedance measurement system of claim 10, wherein the third electrode is a third electrode pair and wherein the second electrode is ground.

13. The impedance measurement system of claim 10, wherein the circuit element is to change a capacitance of the third electrode to adjust the gain and modify the electromagnetic field.

14. The impedance measurement system of claim 10, wherein the circuit element configured to adjust the gain at the third electrode is one of an amplifier and an impedance device.

15. The impedance measurement system of claim 14, wherein the impedance device is at least one of a resistor and a capacitor.

16. The impedance measurement system of claim 10, further comprising an ammeter for measuring a current on the first electrode, wherein the processor detects the presence of the analyte based in part on the current measurement.

17. The impedance measurement system of claim 16, wherein the circuit element configured to adjust the gain at the third electrode adjusts the gain based at least in part on the current measurement.

18. The impedance measurement system of claim 10, further comprising a voltmeter for measuring a voltage at the first electrode, wherein the processor detects the presence of the analyte based in part on the voltage measurement.

19. The impedance measurement system of claim 18, wherein the circuit element configured to adjust the gain at the third electrode adjusts the gain based at least in part on the voltage measurement.

20. A method detecting an analyte in a sample using impedance measurements, comprising:
- receiving the sample at a detection device;
- generating an electromagnetic field between first and second electrodes in the detection device, wherein the first electrode has a first potential and the second electrode has a second potential and wherein the first potential is different from the second potential;
- electrically controlling a third electrode in the detection device to modify the electromagnetic field, steering the electromagnetic field between the first and second electrodes upwards towards the sample, wherein the third electrode has a third potential, and wherein third potential is different from each of the first and second potentials; and
- detecting a presence of the analyte in the sample, based at least in part on a property of the electromagnetic field.

\* \* \* \* \*